(12) United States Patent  
Keglovich et al.

(10) Patent No.: US 9,119,669 B2  
(45) Date of Patent: Sep. 1, 2015

(54) MEDICAL TRACKING SYSTEM USING A GAMMA CAMERA

(75) Inventors: Mike Keglovich, St. Petersburg, FL (US); Christoph Pedain, Munich (DE)

(73) Assignee: Brainlab AG, Feldkirchen (DE)

( * ) Notice: Subject to any disclaimer, the term of this patent is extended or adjusted under 35 U.S.C. 154(b) by 2101 days.

(21) Appl. No.: 11/562,753

(22) Filed: Nov. 22, 2006

(65) Prior Publication Data

US 2007/0167712 A1   Jul. 19, 2007

Related U.S. Application Data

(60) Provisional application No. 60/754,512, filed on Dec. 28, 2005.

(30) Foreign Application Priority Data

Nov. 24, 2005   (EP) .................................. 05025626

(51) Int. Cl.
- *A61B 6/00* (2006.01)
- *A61B 19/00* (2006.01)
- *A61B 6/12* (2006.01)

(52) U.S. Cl.
CPC ............. *A61B 19/5244* (2013.01); *A61B 6/12* (2013.01); *A61B 6/4258* (2013.01); *A61B 19/52* (2013.01); *A61B 19/54* (2013.01); *A61B 19/5212* (2013.01); *A61B 2019/5227* (2013.01); *A61B 2019/5231* (2013.01); *A61B 2019/5255* (2013.01); *A61B 2019/5289* (2013.01); *A61B 2019/542* (2013.01); *A61B 2019/547* (2013.01); *A61B 2019/5483* (2013.01)

(58) Field of Classification Search
USPC .................. 600/411, 424, 426, 427, 436; 250/363.02
See application file for complete search history.

(56) References Cited

U.S. PATENT DOCUMENTS

| | | | |
|---|---|---|---|
| 5,445,150 A * | 8/1995 | Dumoulin et al. ............ 600/424 |
| 5,810,806 A * | 9/1998 | Ritchart et al. ................ 606/45 |
| 6,073,043 A * | 6/2000 | Schneider ..................... 600/424 |
| 6,076,008 A * | 6/2000 | Bucholz ........................ 600/427 |
| 6,374,134 B1 * | 4/2002 | Bladen et al. ................. 600/424 |
| 6,427,079 B1 * | 7/2002 | Schneider et al. ............ 600/424 |
| 6,429,431 B1 * | 8/2002 | Wilk ......................... 250/363.02 |
| 6,522,907 B1 * | 2/2003 | Bladen et al. ................. 600/407 |
| 6,567,687 B2 * | 5/2003 | Front et al. .................... 600/426 |
| 6,587,710 B1 | 7/2003 | Wainer |
| 6,674,916 B1 * | 1/2004 | Deman et al. ................. 382/276 |
| 6,678,546 B2 * | 1/2004 | Toker et al. ................... 600/436 |
| 2002/0065461 A1 * | 5/2002 | Cosman ........................ 600/426 |
| 2004/0015075 A1 | 1/2004 | Kimchy et al. |
| 2004/0054248 A1 * | 3/2004 | Kimchy et al. .................. 600/3 |
| 2004/0127788 A1 * | 7/2004 | Arata ............................ 600/424 |

(Continued)

FOREIGN PATENT DOCUMENTS

DE   196 39 615 C2   10/1999
EP   1 554 987 A1    7/2005

(Continued)

*Primary Examiner* — Mark Remaly

(74) *Attorney, Agent, or Firm* — Tucker Ellis LLP

(57) ABSTRACT

A medical tracking system includes a localization system operative to spatially localize medical instruments; a computer operative to assign absolute and/or relative positions of said instruments in a coordinate system; and at least one localizable gamma camera operative to detect gamma radiation emitted from a tracer material.

13 Claims, 1 Drawing Sheet

(56) References Cited

U.S. PATENT DOCUMENTS

2004/0138555 A1* 7/2004 Krag et al. .................... 600/424
2004/0204646 A1* 10/2004 Nagler et al. ................. 600/424

FOREIGN PATENT DOCUMENTS

| WO | 01/79884 A2 | 10/2001 |
|---|---|---|
| WO | 2005/012945 A1 | 2/2005 |

* cited by examiner

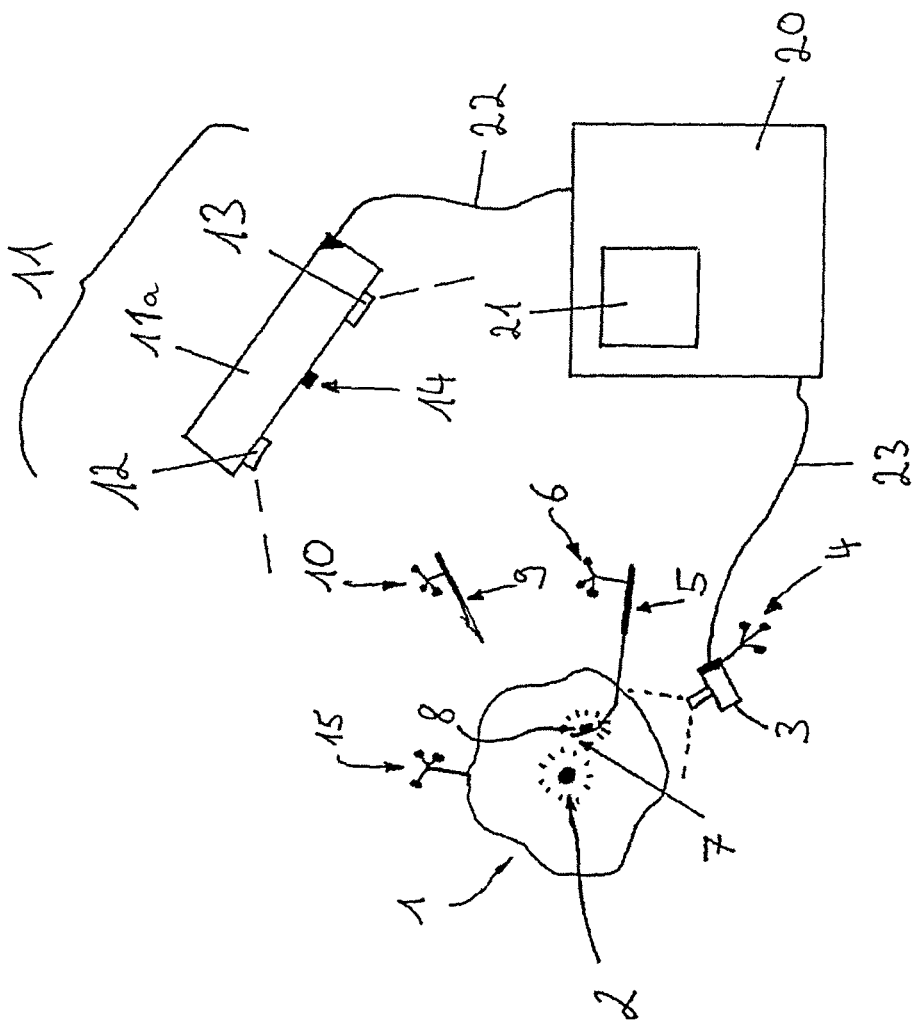

MEDICAL TRACKING SYSTEM USING A GAMMA CAMERA

RELATED APPLICATION DATA

This application claims priority of U.S. Provisional Application No. 60/754,512 filed on Dec. 28, 2005, which is incorporated herein by reference in its entirety.

FIELD OF THE INVENTION

The present invention relates to the tracking of objects, such as medical instruments and/or bodies, in a medical environment.

BACKGROUND OF THE INVENTION

An exemplary medical navigation and tracking system is disclosed in DE 196 39 615 C2. Various forms of intraoperative imaging coupled with navigation are becoming standardized in today's medical environment. This trend will continue to grow in various fields, including tumor/tissue resection, patient positioning, and confirmation of planned trajectories. Some current forms of intraoperative imaging include CT and MRI; however, these diagnostic tools and subsequent images are neither real time nor precise enough to locate certain abnormalities, particularly in deep tissue areas. Although ultrasound provides real time intraoperative imaging, depth and resolution of images can be limited with current ultrasound technology.

SUMMARY OF THE INVENTION

A medical tracking system includes a localization system for spatially localizing medical instruments, and a computer assigning absolute and/or relative positions of said instruments in a coordinate system. The tracking system further includes at least one localizable gamma camera for detecting gamma radiation emitted from a tracer material.

An imaging modality using gamma rays combined with a tracking/navigation system can be used intraoperatively. Gamma ray technology can provide benefits not previously offered with other intraoperative treatment pathways. Gamma rays are one of three sources of radioactive radiation. The other two sources are alpha and beta rays, each having distinctly different properties and characteristics than gamma rays. Some characteristics of gamma raidiation include the following:
- gamma radiation consists of pure energy;
- gamma radiation is photon based;
- gamma radiation is able to travel long distances and easily penetrate through objects.

On this basis, a gamma camera can provide functional real time intraoperative imaging. Advantageously, the gamma camera allows a surgeon to see anatomical structures, soft tissue and abnormalities as they appear within the body at a particular moment in time. Additionally, the real time imaging can display a surgical instrument within a region of interest, and the surgeon also can verify complete resection of tissue/tumors.

When using gamma camera/ray technology, the camera can be portable, similar to an adaptable surgical tool, and can obtain images much faster and in real time relative to conventional imaging systems. Using the gamma camera, costly operating room time is not spent repositioning patients into an intraoperative CT scanner or MRI during intraoperative imaging.

The medical tracking system can include a camera based localization system having a video camera system, an infrared camera system, or both. The camera system can define or be used to define a coordinate system. Further, the medical tracking system can include an electromagnetic localization system that creates an electromagnetic field in which objects can be localized, wherein the electromagnetic field can define a coordinate system. The coordinate system may be defined on the basis of determined positions of the gamma camera and/or one or more of the localized instruments.

The medical tracking system can include instrument markers detectable by the gamma camera. Moreover, said gamma camera may carry tracking markers by means of which the camera itself can be spatially localized and/or identified by the tracking system.

A medical navigation system can include a tracking system as described herein. Such a medical navigation system may include a memory device storing images obtained by the gamma camera. The medical navigation system can include an image output device for displaying images obtained by the gamma camera, in particular together with one or more of the following:
- spatially assigned or registered patient image data, such as CT or MR data;
- spatially assigned or registered instruments or their positional data;
- instruments localized by the gamma camera; and
- the gamma camera itself.

The gamma camera may be applied to a tracking method in a medical environment, wherein the method includes the spatial localization of medical instruments and the computer assisted assignment of absolute and/or relative positions of the instruments in a coordinate system. The method also can include the localization of a at least one localizable gamma camera, the camera operable to detect gamma radiation emitted from a tracer material.

At least one of the following coordinate systems can be used:
- a coordinate system defined by a camera based localization system having a video camera system or an infrared camera system or both;
- a coordinate system defined by an electromagnetic localization system creating an electromagnetic field in which objects can be localized; and/or
- a coordinate system defined on the basis of determined positions of the gamma camera and/or one or more of the localized instruments.

Also, at least two of the coordinate systems may be used in combination and correlated with each other in the localization of instruments and/or the gamma camera in order to create a multi-modal tracking system.

An image or images made by the gamma camera can be used in an image guided surgery system, a medical navigation system, and/or a surgical/medical planning system performing or planning at least one of the following tasks:
- displaying images made by the gamma camera;
- storing images made by the gamma camera;
- creating patient image data sets from images made by the gamma camera;
- spatially assigning or registering previously acquired patient image data, such as CT or MR data to the images made by the gamma camera;
- spatially assigning or registering instruments or their positional data to the images made by the gamma camera;
- displaying the instruments localized by the gamma camera or the gamma camera itself in positional relationship to the image data sets created or acquired;

displaying the tracer material in selectively enriched regions of interest, in particular together with information relevant to a medical procedure and/or with information relevant to the positioning of an instrument.

Any images made by the gamma camera may be used not only for real time navigation, but also for planning a subsequent therapy.

An instrument or a part of an instrument can be localized by detecting a tracer material irradiating gamma energy, in particular a radioactive material on said instrument by means of said gamma camera.

Further, before the method is carried out and independently from all steps of the method, radioactive tracer material can be injected into the patient. This tracer material can be selectively enriched based on properties of the different body portions, such as based on molecular binding, for example.

The handheld gamma camera can be positioned over a region of interest (ROI) of the patient. The radioactive tracer material emits energy within the ROI, and the camera collects the photons emitted from the tracer material to produce an image. This image can now be displayed in a navigation system. The navigation system, in real time, then can reconstruct multiple images taken from different angles to a three-dimensional image and can show the three-dimensional image predicated on the spatial relation between the camera and patient location. Although not limited to this, the technology can be used in such modalities and treatments as breast tumors, melanoma, prostate cancer, kidney metastasis, and lung metastasis for precise diagnosis and tracking of the target volume during a surgical procedure.

The camera can be used to track instruments or markers introduced into the body. In such application, the gamma camera can act as an instrument tracking extension that provides to the current system "x-ray vision". In this application, the position and orientation of the gamma camera can be determined by the navigation system and the spatial information about the tracking markers can be used to correlate the position of various markers with each other. This application is possible using one or more gamma cameras, either mounted in a fixed and known location and orientation, or tracked with another tracking system.

The gamma camera can thus be used as a tracking system to track the instruments and/or the targeted area. This expands the application of the technology to a true simultaneous tracking technique for moving instruments and moving target areas.

BRIEF DESCRIPTION OF THE DRAWINGS

The forgoing and other features of the invention are hereinafter discussed with reference to the drawing.

FIG. 1 shows a schematic representation of an exemplary tracking system in accordance with the present invention.

DETAILED DESCRIPTION

FIG. 1 is a schematic diagram showing a patient's body part 1 including a gamma radiant tracer material 2 within a region of interest, wherein a gamma camera 3 captures data from the patient's body part 1. First, second, third and fourth tracking arrays (e.g., arrays of reflective spheres) 4, 6, 10 and 15 are coupled to the gamma camera 3, a first instrument 5, a second instrument 9, and the patient's body part 1, respectively. The first instrument 5 includes a flexible tip section 7 having a tracer material 8 on the tip section 7. The second instrument 9 is a rigid instrument such as a scalpel, for example. An infrared tracking system 11 includes first and second stereoscopic infrared tracking cameras 12 and 13, each coupled to a camera holder 11a. An infrared light source 14 is coupled to the camera holder 11a. A navigation system 20, which includes a display 21, is operatively coupled to the infrared tracking system 11 and gamma camera 3 via lines 22 and 23, respectively. Gamma camera 3, instrument 5 and scalpel 9 can be tracked by the infrared tracking system 11 and navigated by navigation system 20 as disclosed in DE 196 39 615 C2, for example.

Injection of radioactive tracer material 2 into the patient 1 typically takes place approximately 45 minutes to 24 hours prior to surgery. The photons within the region of interest are reflected back to the camera 3 by use of this radioactive tracer material 2. The amount of photons is not large enough to negatively affect the medical team participating in the procedure, although protection through the use of lead vests and protective glasses may be utilized.

Reflective arrays 4 and 15 are positioned in the pre-calibrated gamma camera 3 and patient body part 1 via universal adapters, for example. Diagnostic images can be loaded into the navigation system 20, and the patient can be registered using known methods. The spatial relationships between instruments 5 and 9, gamma camera 3, and patient 1 are coordinated via the navigation system 20 through the arrays 4, 6, 10, 15 and displayed on the navigation display 21.

Since the pre-calibrated gamma camera 3 is tracked, i.e., localized by tracking system 11 through reflective array 4, the content of the images obtained by the camera also can be positionally assigned, and those images can supplement the diagnostic image information previously obtained (e.g., from previously obtained images of the patient and/or patient body part via other imaging modalities) and loaded into the navigation system 20. The gamma camera images can be obtained in real time, and surgeons can view anatomical regions and shapes and are able to identify abnormalities as they appear within the body intraoperatively.

Additionally, the surgeon can view surgical instruments 5 and 9 approaching and/or acting on tissue, and verify complete resection. With respect to the instrument 5 that includes the flexible tip section 7, the infrared tracking system may not be able to provide exact information about the tip's location in the body portion 1. To make up for this lack of information, instrument 5 is equipped with tracer material 8 at its tip section 7 and, thus, the tip section 7 can be localized by the gamma camera 3 and correctly represented by the navigation system.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical tracking system, comprising:
   a localization system operative to define a coordinate system and to detect position signals from a marker device which indicate the position of the marker device;
   a computer operative to assign positions to medical instruments in the coordinate system, wherein the computer is operatively coupled to the localization system;
   at least one localizable gamma camera operative to detect gamma radiation emitted from a tracer material, wherein the gamma camera is operatively coupled to the computer;
   wherein the marker device is attached to the gamma camera in a fixed positional relationship relative to the gamma camera, wherein the position of the gamma camera in the coordinate system is assignable by the computer based on the position signals detected by the localization system;
   at least one medical instrument including a marker attached thereto, wherein the marker attached to the medical instrument contains a tracer material which emits gamma energy and wherein the marker attached to the medical instrument is positionally fixed relative to the at least one medical instrument and detectable by the gamma camera,
   wherein the computer is operative to assign, based on the gamma radiation emitted from the marker which emits gamma energy and detected by the gamma camera, and based on the position of the gamma camera determined by the position signals detected by the localization system, a position to the marker which emits gamma energy.

2. The medical tracking system of claim 1, wherein the localization system comprises a camera based localization system utilizing at least one of a video camera system or an infrared camera system, said camera system defining said coordinate system.

3. The medical tracking system of claim 1, wherein the localization system comprises an electromagnetic localization system operative to create an electromagnetic field in which objects can be localized, said electromagnetic field defining said coordinate system.

4. A medical navigation system comprising the medical tracking system of claim 1.

5. The medical navigation system of claim 4, further comprising a memory device operable to store images obtained by said gamma camera.

6. The medical navigation system of claim 4, further comprising an image output for displaying images obtained by said gamma camera together with at least one of:
   spatially assigned or registered patient image data;
   spatially assigned or registered instruments or their positional data;
   instruments localized by said gamma camera; or
   said gamma camera itself.

7. The medical navigation system of claim 6, wherein the image output is operative to display patient image data that includes CT image data or MR image data.

8. A tracking method in a medical environment, comprising:
   spatially localizing at least one gamma camera by detecting, using a localization system, the position of a marker device attached to the gamma camera in a fixed positional relationship relative to the gamma camera, said gamma camera operative to detect gamma radiation emitted from a tracer material;
   assigning via computer assistance positions of said gamma camera in a coordinate system based on the detected position of the marker device; and
   using the detected position of the marker device to localize an instrument or a part of an instrument by detecting, using the gamma camera, a marker which emits gamma energy and is attached to and positionally fixed relative to said instrument and by using the detection results received from the gamma camera to determine the position of the tracer material relative to the gamma camera.

9. The tracking method of claim 8, wherein assigning includes using at least one of:
   a coordinate system defined by a camera based localization system having at least one video camera system or infrared camera system;
   a coordinate system defined by an electromagnetic localization system creating an electromagnetic field in which objects can be localized; or
   a coordinate system defined on the basis of determined positions of said gamma camera or one or more of said localized instruments.

10. The tracking method of claim 9, wherein assigning includes using at least two of said coordinate systems in combination, and correlating between the at least two coordinate systems in the localization of instruments or said gamma camera to create a multi-modal tracking system.

11. The tracking method of claim 8, further comprising using an image or images captured by the gamma camera in an image guided surgery system, a medical navigation system or a medical planning system performing or planning at least one of the following:
   displaying images captured by the gamma camera;
   storing images captured by the gamma camera;
   creating patient image data sets from images captured by the gamma camera;
   spatially assigning or registering previously acquired patient image data to the images captured by the gamma camera;
   spatially assigning or registering instruments or their positional data to the images captured by the gamma camera;
   displaying said instruments localized by said gamma camera or said gamma camera itself in positional relationship to said created or acquired image data sets;
   displaying said tracer material in selectively enriched regions of interest.

12. The method of claim 11, wherein spatially assigning or registering previously acquired patient image data includes using CT image data or MR image data as the patient image data.

13. The tracking method of claim 11, wherein displaying said instruments includes displaying the instruments together with at least one of information relevant to a medical procedure and information relevant to the positioning of an instrument.

* * * * *